United States Patent
Han et al.

(10) Patent No.: US 8,652,815 B2
(45) Date of Patent: Feb. 18, 2014

(54) TRANSFORMANT COMPRISING GENE CODING FOR WS/DGAT AND METHOD OF PRODUCING FATTY ACID ETHYL ESTERS USING THE SAME

(75) Inventors: Sung Ok Han, Seoul (KR); Kyung-Ok Yu, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 202 days.

(21) Appl. No.: 13/165,636

(22) Filed: Jun. 21, 2011

(65) Prior Publication Data

US 2012/0149074 A1   Jun. 14, 2012

(30) Foreign Application Priority Data

Dec. 8, 2010   (KR) .................. 10-2010-0125018

(51) Int. Cl.
| | |
|---|---|
| *C12P 7/64* | (2006.01) |
| *C12N 9/00* | (2006.01) |
| *C12N 1/20* | (2006.01) |
| *C12N 15/00* | (2006.01) |
| *C07H 21/04* | (2006.01) |

(52) U.S. Cl.
USPC ..... 435/134; 435/183; 435/252.3; 435/320.1; 536/23.2

(58) Field of Classification Search
None
See application file for complete search history.

(56) References Cited

PUBLICATIONS

Chica et al. Curr Opin Biotechnol. Aug. 2005;16(4):378-84.*
Sen et al. Appl Biochem Biotechnol. Dec. 2007;143(3):212-23.*
Wang et al. Yeast. Dec. 2002;19(16):1447-58.*
Accession Q8GGG1. Mar. 1, 2003.*
Accession AF529086. Mar. 3, 2003.*
Accession P14065. Jan. 1, 1990.*
Accession X96740. Nov. 14, 2006.*
Accession P54838. Oct. 1, 1996.*
Accession Z38114. Apr. 18, 2005.*
Accession P53154. Oct. 1, 1996.*
Accession Z72606. Aug. 11, 1997.*

* cited by examiner

*Primary Examiner* — Christian Fronda
(74) *Attorney, Agent, or Firm* — Swanson & Bratschun L.L.C.

(57) ABSTRACT

The present invention relates to a transformant comprising a gene encoding ws/dgat (wax ester synthase/acyl-coenzyme A: diacylglycerol acyltransferase) and a method of producing fatty acid ethyl esters using the same. Specifically, the transformant for producing fatty acid ethyl esters is constructed such that glycerol is used as a fermentation substrate, and comprises an atfA gene encoding ws/dgat (wax ester synthase/acyl-coenzyme A: diacylglycerol acyltransferase) from *Acinetobacter* sp., so that the atfA gene is expressed in the transformant.

6 Claims, 8 Drawing Sheets

TRANSFORMANT COMPRISING GENE CODING FOR WS/DGAT AND METHOD OF PRODUCING FATTY ACID ETHYL ESTERS USING THE SAME

TECHNICAL FIELD

The present invention relates to a transformant, which uses glycerol as a fermentation substrate and can produce fatty acid ethyl esters by expressing a ws/dgat-encoding gene therein, and to a method of producing fatty acid ethyl esters using the transformant.

BACKGROUND ART

Since the United Nations Conference on Environment and Development (UNCED) in Rio de Janeiro in 1992 and the Kyoto Convention in 1997, the emission of air pollutants has been regulated, and biofuel has received a great deal of attention as a renewable energy source for reducing the emission of carbon dioxide. Currently, there is an urgent need to develop biodiesel that can be used as a clean alternative fuel for diesel vehicles, which account for 30% or more of transportation vehicles in the world and generate 50% or more air pollution. Biodiesel is made from organic materials by esterifying animal and vegetable oils with alcohols such as methanol or ethanol and removing glycerol from the esterified oils, thus obtaining fatty acid methyl esters or fatty acid ethyl esters. Biodiesel has properties similar to petroleum-derived light oil and causes little air pollution upon combustion, and thus when it is mixed with petroleum-based light oil, it can be used as a clean alternative fuel that can significantly reduce vehicle air pollution, which is the main cause of air pollution. Thus, the demand and need for biodiesel is increasing. In addition to an alternative fuel for light oil, biodiesel can be used as raw materials and additives for lubricant oils and can also be used in various applications, including pollution-free solvents and agricultural biochemicals. In addition, biodiesel can also be used as a catalyst to promote bioremediation for cleaning the seashore when contaminated with crude oils. So far, biodiesel has been produced from a variety of animal and vegetable oils by chemical catalytic methods using a strong acid or a strong base. However, in the chemical catalytic methods, a multistep reaction process that consumes large amounts of energy is required, it is difficult to recover catalysts and byproducts, and a large amount of wastewater is generated, thus causing secondary environmental contamination. Due to these problems, a low-energy-consuming, environmentally friendly new biological process that can satisfy the strong demand for biodiesel is required. In 2006, Rainer et al. reported the production of fatty acid ethyl esters in *E. coli* (Rainer Kalscheuer et al, Microbiology. 152, 2529-2536, 2006), suggesting that fatty acid ethyl esters can be processed by a biological method. However, the production of alcohols such as ethanol in *E. coli* is insignificant, and *E. coli* has low resistance to alcohols. In recent years, studies on the increase in the production of fatty acid ethyl esters in *E. coli* have been conducted by Eric et al. (Eric J. Steen et al., Nature. 463. 559-556, 2010), but even in an *E. coli* strain transformed such that ethanol can be produced therein, the production of ethanol was significantly low. This led to a study that reported an increase in the production of fatty acid ethyl esters when ethanol was added to a medium. The present inventors have developed a more efficient system for producing fatty acid ethyl esters as a result of selecting yeast having ethanol resistance and high ethanol productivity as a host for producing fatty acid ethyl esters.

Also, glycerol ($C_3H_8O_3$), which is used as a substrate in the present invention, is chemically more reduced than glucose ($C_6H_{12}O_6$), and thus provides a higher reducing power for the metabolism of microorganisms. Since a lot of materials produced during fermentation are generally required to have reducing power in their metabolism, the use of glycerol as a substrate can lead to a significant improvement in the yield and productivity of desired fermentation products. Currently, as the production of biodiesel increases, the production of glycerol also increases, and thus the price thereof is decreasing rapidly. As described above, because a rapid increase in the production of biodiesel leads to an increase in the production of the byproduct glycerol, the effective treatment of byproducts including glycerol will be issued. Thus, if glycerol can be effectively used to produce useful fermentation products, it can provide a lot of additional effects.

DISCLOSURE

Technical Problem

It is an object of the present invention to provide a transformant for producing fatty acid ethyl esters that comprises a gene encoding ws/dgat (wax ester synthase/acyl-coenzyme A: diacylglycerol acyltransferase), a glycerol dehydrogenase gene, a dihydroxyacetone kinase gene and a glycerol uptake protein gene, and a method for preparing the transformant.

Another object of the present invention is to provide a method for producing fatty acid ethyl esters using said transformant.

Technical Solution

To achieve the above objects, the present invention provides a transformant for producing fatty acid ethyl esters, which comprises a gene encoding ws/dgat (wax ester synthase/acyl-coenzyme A: diacylglycerol acyltransferase), a glycerol dehydrogenase gene, a dihydroxyacetone kinase gene and a glycerol uptake protein gene.

The present invention also provides a method for preparing a transformant for preparing fatty acid ethyl esters, the method comprising the steps of: constructing a recombinant vector comprising a gene encoding ws/dgat (wax ester synthase/acyl-coenzyme A: diacylglycerol acyltransferase) and a glycerol uptake protein gene; constructing a recombinant vector comprising a glycerol dehydrogenase gene and a dihydroxyacetone kinase gene; and transforming the recombinant vectors.

The present invention also provides a method for producing fatty acid ethyl esters, the method comprising a step of culturing said transformant using glycerol as a substrate.

Advantageous Effects

The transformant according to the present invention is constructed so that it uses glycerol as a carbon source and contains genes causing the synthesis of fatty acid ethyl esters. Accordingly, the transformant of the present invention can be used to produce large amounts of fatty acid ethyl esters using glycerol, which is a byproduct of biodiesel production, and thus is highly useful.

BRIEF DESCRIPTION OF DRAWINGS

In FIG. 1, lane 1: 1-kb DNA marker; and lane 2: Ws/dgat PCR product.

FIG. 2 shows the results of performing agarose gel electrophoresis of PCR products, wherein

In FIGS. 5a and 5b, lane 1: YPH499 (pESC-TRP); lane 2: YPH499 (pGcyaDak, pGup1aWS.DGATcas); ♦: YPH499 (pESC-TRP); ■: YPH499 (pGcyaDak,pGupCas); and ▲: YPH499 (pGcyaDak, pGup1a ws.dgat cas).

MODE FOR INVENTION

Figure 1:
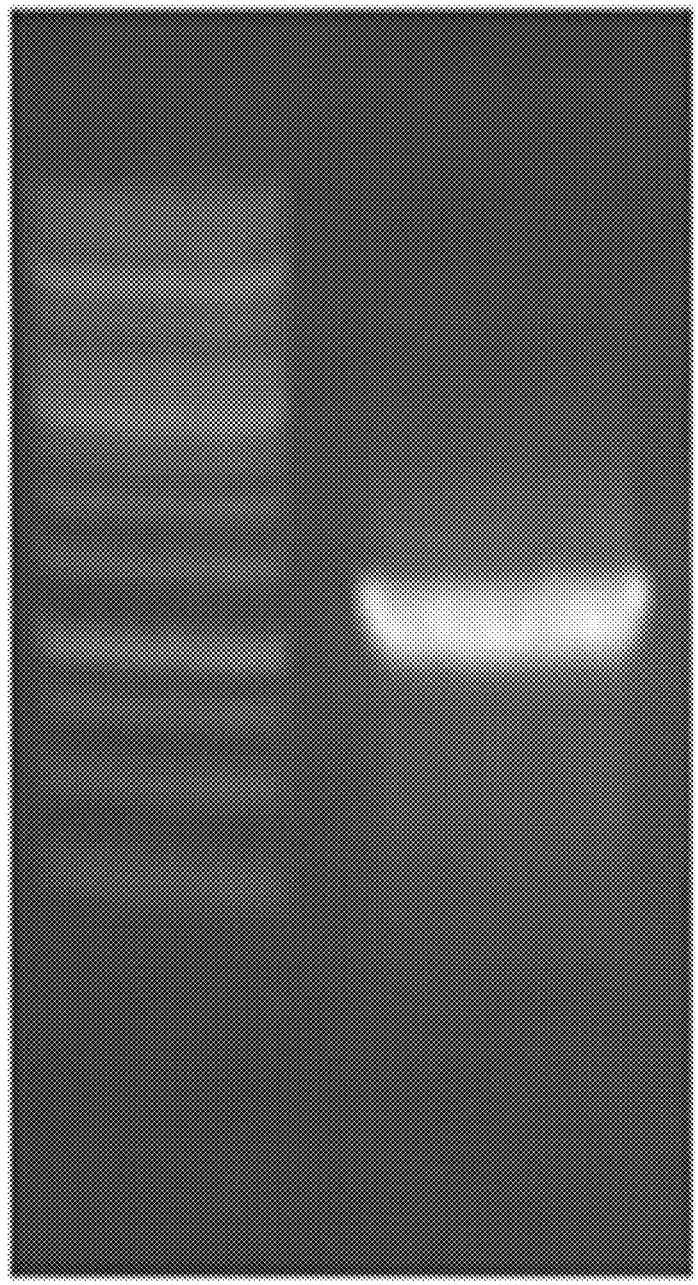
FIG. 1 shows the results of performing agarose gel electrophoresis of the PCR product of the ws/dgat-encoding gene in the present invention.

The present invention relates to a transformant for producing fatty acid ethyl esters, which comprises a gene encoding ws/dgat (wax ester synthase/acyl-coenzyme A: diacylglycerol acyltransferase), a glycerol dehydrogenase gene, a dihydroxyacetone kinase gene and a glycerol uptake protein gene.

In the present invention, the ws/dgat-encoding gene is preferably a gene from *Acinetobacter* sp., but is not limited thereto.

The present invention, the ws/dgat preferably has the amino acid sequence set forth in SEQ ID NO: 1, but may also be a mutant protein having ws/dgat activity, which contains at least one mutation (such as a substitution, deletion or addition) in the amino acid sequence of SEQ ID NO: 1.

In the present invention, the gene encoding ws/dgat preferably has the nucleotide sequence set forth in SEQ ID NO: 2, but may also be a gene having a homology of 80% or greater, preferably 85% or greater, even more preferably 90% or greater, and most preferably 95% or greater, with the nucleotide sequence of SEQ ID NO: 2, in view of the degeneracy of the genetic code.

In one embodiment of the present invention, the glycerol dehydrogenase preferably has the amino acid sequence set forth in SEQ ID NO: 3, but may also be a mutant protein having glycerol dehydrogenase activity, which contains at least one mutation (such as a substitution, deletion or addition) in the amino acid sequence of SEQ ID NO: 3.

In one embodiment of the present invention, the glycerol dehydrogenase gene preferably has the nucleotide sequence set forth in SEQ ID NO: 4, but may also be a gene having a homology of 80% or greater, preferably 85% or greater, even more preferably 90% or greater, and most preferably 95% or greater, with the nucleotide sequence of SEQ ID NO: 4, in view of the degeneracy of the genetic code.

In another embodiment of the present invention, the dihydroxyacetone kinase preferably has the amino acid sequence set forth in SEQ ID NO: 5, but may also be a mutant protein having dihydroxyacetone kinase activity, which contains at least one mutation (such as a substitution, deletion or addition) in the amino acid sequence of SEQ ID NO: 5.

In still another embodiment of the present invention, the dihydroxyacetone kinase gene preferably has the nucleotide sequence set, forth in SEQ ID NO: 6, but may also be a gene having a homology of 80% or greater, preferably 85% or greater, even more preferably 90% or greater, and most preferably 95% or greater, with the nucleotide sequence of SEQ ID NO: 6, in view of the degeneracy of the genetic code.

In still another embodiment of the present invention, the glycerol uptake protein preferably has the amino acid sequence set forth in SEQ ID NO: 7, but may also be a mutant protein having glycerol uptake activity, which contains at least one mutation (such as a substitution, deletion or addition) in the amino acid sequence of SEQ ID NO: 7.

In still another embodiment of the present invention, the glycerol uptake protein gene preferably has the nucleotide sequence set forth in SEQ ID NO: 8, but may also be a gene having a homology of 80% or greater, preferably 85% or greater, even more preferably 90% or greater, and most preferably 95% or greater, with the nucleotide sequence of SEQ ID NO: 8, in view of the degeneracy of the genetic code.

The transformant of the present invention is yeast, and preferably *Saccharomyces cerevisiae*, but the scope of the present invention is not limited thereto.

The transformant of the present invention is preferably, but not limited to, the yeast *Saccharomyces cerevisiae* YPH499 (pGcyaDak, pGup1a ws.dgat cas) deposited under accession number KCCM11094P. *Saccharomyces cerevisiae* YPH499 (pGcyaDak, pGup1a ws.dgat cas) has been deposited at the Korean Culture Center of Microorganisms, at 361-221, Yurim B/D, Hongje-1-dong, Seodaemun-gu, Seoul, 120-091, Republic of Korea, on Aug. 18, 2010 and given the deposit reference KCCM11094P. This deposit was made under the Budapest Treaty on the International Recognition of the Deposit of Microorganisms, and all restrictions imposed by the depositor on the availability to the public of the deposited material will be irrevocably removed upon the grant of the patent.

Also, the present invention relates to a method for preparing a transformant for preparing fatty acid ethyl esters, the method comprising the steps of: constructing a recombinant vector comprising a gene encoding ws/dgat (wax ester synthase/acyl-coenzyme A: diacylglycerol acyltransferase) and a glycerol uptake protein gene; constructing a recombinant vector comprising a glycerol dehydrogenase gene and a dihydroxyacetone kinase gene; and transforming the recombinant vectors.

As used herein, the term "recombinant vector" describes a vector capable of expressing a target protein in a suitable host cell, and refers to a genetic construct that comprises essential regulatory elements to which a gene insert is operably linked in such a manner as to be expressed in a host cell. Examples of the vector include, but are not limited to, a plasmid vector, a cosmid vector, a bacteriophage vector and a viral vector. Suitable expression vectors may include a signal sequence or a leader sequence for membrane targeting or secretion, as well as regulatory sequences such as a promoter, an operator, an initiation codon, a termination codon, a polyadenylation signal, an enhancer and the like, and can be prepared in various ways depending on the desired purpose. The promoter of the vector may be constitutive or inducible. Further, the expression vector may include one or more selective markers for selecting a host cell containing the expression vector, and, in the case of a replicable expression vector, may include a nucleotide sequence of replication origin.

Also, the recombinant vector may further have a fragment for regulating expression, which has a variety of functions for suppression, amplification or triggering of expression, as well as a marker for the selection of a transformant, a antibiotic resistance gene, or a gene encoding a signal for extracellular secretion.

The recombinant vector comprising the gene encoding ws/dgat (wax ester synthase/acyl-coenzyme A: diacylglycerol acyltransferase) and the glycerol uptake protein gene may be, for example, pGup1a ws.dgat cas, but is not limited thereto.

The recombinant vector comprising the glycerol dehydrogenase gene and the dihydroxyacetone kinase gene may be, for example, pGcyaDak, but is not limited thereto.

When yeast is used as a host in the present invention, the expression vector may be, for example, a YEpl3, YCp50, pRS or pYEX vector, and the promoter may be, for example, a GAL promoter or an ADD promoter.

Transformation in the present invention may be carried out according to any method for introducing a nucleic acid molecule into an organism, a cell, a tissue or an organ, and methods that may be used to introduce recombinant DNA into yeast include electroporation (Method Enzymol., 194, 182-187 (1990)), the spheroplast method (Proc. Natl. Acad. Sci. USA, 84, 1929-1933 (1978)), and the lithium acetate method (J. Bacteriol., 153, 163-168 (1983)).

The present invention also relates to a method for producing fatty acid ethyl esters, which comprise a step of culturing the transformant of the present invention using glycerol as a substrate.

In the present invention, glycerol is preferably glycerol that is a byproduct of glycerol production, but is not limited thereto.

In the process of producing fatty acid ethyl esters according to the present invention, a fatty acid salt having 12 to 20 carbon atoms is preferably added to a medium, but the scope of the present invention is not limited thereto.

The transformant is preferably yeast, more preferably yeast *Saccharomyces cerevisiae*, and more preferably *Saccharomyces cerevisiae* YPH499 (pGcyaDak, pGup1a ws.dgat cas) [accession number: KCCM11094P].

As used herein, the term "composition for producing fatty acid ethyl esters" means, for example, a composition capable of producing fatty acid ethyl esters by culturing the transformant using glycerol as a substrate. The composition may include a polypeptide, a fermentation broth, a cell lysate, a purified or non-purified yeast extract or the like, that is suitable for the production of fatty acid ethyl esters.

The transformant of the present invention may be cultured using any conventional method that is used for the culture of hosts.

The culture of the transformant may be carried out using any conventional method for microbial culture, including a batch culture method, a fed-batch culture method, a continuous culture method, and a reactor-type culture method.

Examples of a medium for culturing the transformant using *E. coli* or yeast as a host include complete media or synthetic media, for example, LB medium, NB medium and the like. Also, the transformant is cultured at a temperature ranging from 25 to 30° C., so as to facilitate the accumulation of ws/dgat in microbial cells.

Examples of the carbon source that may be used for the growth of microorganisms include sugars, such as glucose, fructose, sucrose, maltose, galactose or starch; lower alcohols, such as ethanol, propanol or butanol; polyhydric alcohols such as glycerol; organic acids, such as acetic acid, citric acid, succinic acid, tartaric acid, lactic acid or gluconic acid; and fatty acids, such as propionic acid, butanoic acid, pentanoic acid, hexanoic acid, heptanoic acid, octanoic acid, nonanoic acid, decanoic acid, undecanoic acid or dodecanoic acid.

Examples of the nitrogen source include ammonium salts, such as ammonia, ammonium chloride, ammonium sulfate or ammonium phosphate, and materials of natural origin, such as peptone, meat juice, yeast extracts, malt extracts, casein hydrolysates, or corn steep liquor. Also, examples of minerals include monopotassium phosphate, dipotassium phosphate, magnesium phosphate, magnesium sulfate, sodium chloride and the like. The medium may be supplemented with antibiotics, such as kanamycin, ampicillin, tetracycline, chloramphenicol and streptomycin.

Also, when microorganisms transformed with an expression vector having an inducible promoter are cultured, an inducer suitable for the kind of promoter may be added to the medium. Examples of the inducer include isopropyl-β-D-thiogalactopyranoside (IPTG), tetracycline, indole acrylic acid (IAA), and the like.

The fatty acid ethyl ester synthase ws/dgat can be obtained by centrifuging the culture medium of the transformant, collecting a cell or a supernatant from the centrifuged medium, and subjecting the collected cell or supernatant to one or a combination of two or more selected from cell lysis, extraction, affinity chromatography, cation or anion exchange chromatography, and gel filtration.

The determination of whether the resulting purified substance is the desired yeast can be performed using a conventional method, for example, SDS-polyacrylamide gel electrophoresis or Western blotting.

In one embodiment of the present invention, the production of fatty acid ethyl esters in *Saccharomyces cerevisiae* is based on short chain fatty acids such as oleic acid, in which oleic acid is converted into Oleoyl-CoA by acyl CoA synthase, and the Oleoyl-CoA reacts with ethanol to produce ethyl oleate ester, the reaction being catalyzed by wax ester synthase.

Accordingly, in the present invention, the ws/dgat-encoding gene from *Acinetobacter* sp. is inserted into a strain constructed such that glycerol is used as the carbon source, whereby the synthesis of fatty acid ethyl esters becomes possible.

Hereinafter, the present invention will be described in further detail with reference to examples, but the scope of the present invention is not limited to these examples.

EXAMPLES

Example 1

Amplification of Ws/Dgat-Encoding Gene from *Acinetobacter*

In order to insert an atfA gene from *Acinetobacter*, which encodes ws/dgat (wax ester synthase/acyl-coenzyme A: diacylglycerol acyltransferase), a PCR reaction was performed using the genomic DNA of *Acinetobacter* sp. as a template and the following pair of primers, each containing a site for the restriction enzyme spel: forward primer (5'-actagtcccgc-cgccaccaaggagatgcgcccattacatccgat-3', SEQ ID NO: 9); and reverse primer (5'-actagtttaattggctgttttaatatcttc-3', SEQ ID NO: 10). The PCR reaction was performed under the following conditions: step 1 at 95° C. for 10 min; step 2 at 95° C. for 30 sec; step 3 at 50° C. for 30 sec; step 4 at 72° C. for 2 min; step 5 at 95° C. for 10 min; the process from step 2 to step 4 being repeated for 30 cycles [1.2 kb PCR product].

Example 2

Cloning and Transformation of Ws/Dgat-Encoding Gene from *Acinetobacter*

The amplification product obtained in Example 1 was electrophoresed on 0.8% agarose gel, and the DNA fragment on the agarose gel was collected using a Biospin gel extraction kit (Bioflux).

Figure 3A:
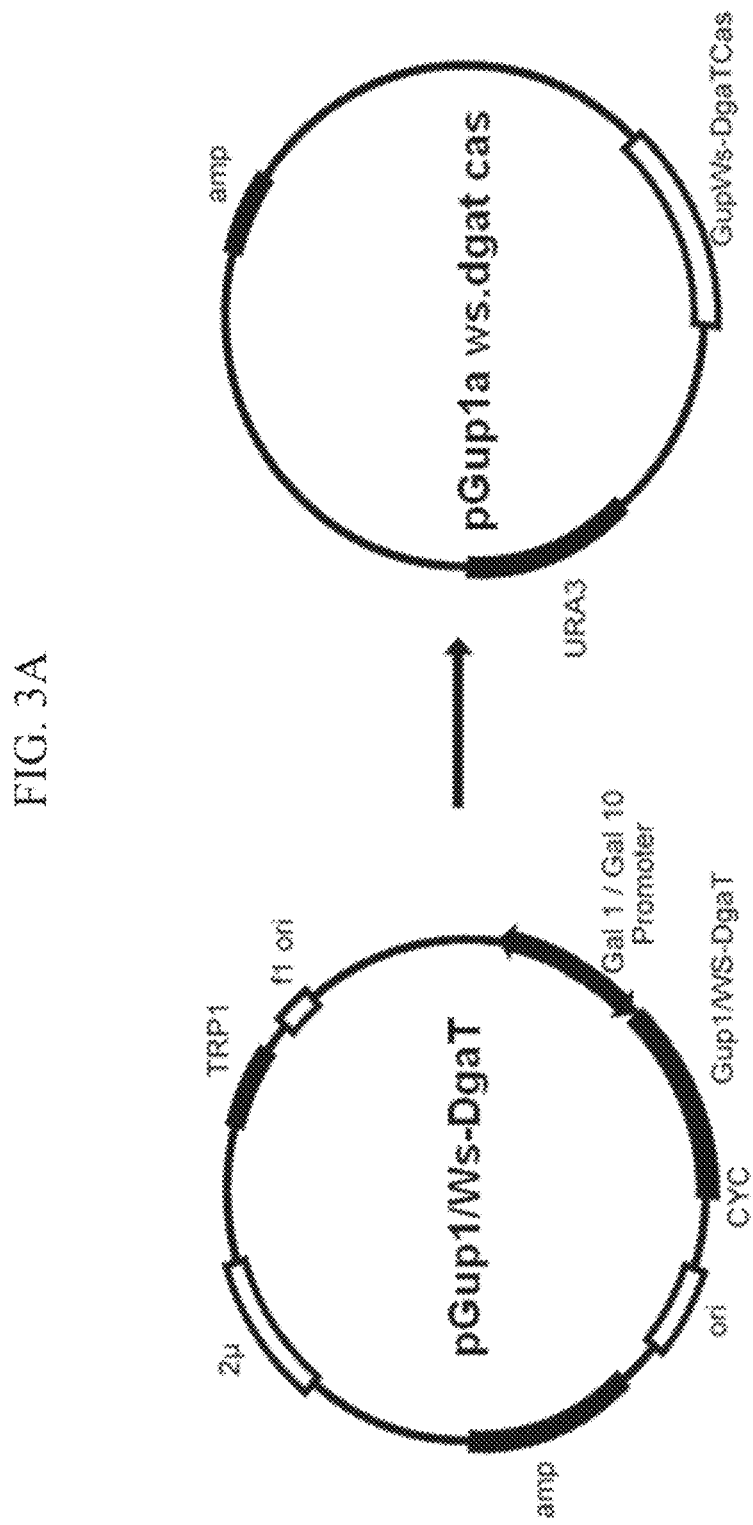
FIG. 3a is a schematic diagram showing the process of constructing the recombinant vector pGup1a ws.dgat cas containing a ws/dgat-encoding gene according to the present invention.

Then, the fragment was digested with the restriction enzyme Spe1, after which it was ligated with pGup1 containing glycerol uptake protein and was transformed into *E. coli* DH5a (Invitrogen). Then, the ligated recombinant plasmid DNA was separated from the transformant. The recombinant vector was named "pGup1/Ws-Dgat" and is shown in FIG. 3a. Also, in order to insert pGup1/Ws-Dgat, a sense primer (5'-ggatccatgtcagcattttaggtaaattccgtg-3'; SEQ ID NO: 11) and an antisense primer (5'-ggatccataatgtcgctgatcagcatc-ctgtct-3'; SEQ ID NO: 12) were constructed so as to include a BamH1 recognition sequence, and were cloned into the yeast integration vector YIP-5 [ATCC], thereby constructing pGup1a ws.dgat cas. This was inserted into the genomic DNA of *Saccharomyces cerevisiae* (FIG. 3a).

Example 3

Transformation of Glycerol Dehydrogenase Gene, Dihydroxyacetone Kinase Gene and Glycerol Uptake Protein Gene 1. Amplification of Glycerol Dehydrogenase Gene, a Dihydroxyacetone Kinase Gene and a Glycerol Uptake Protein Gene In order to efficiently convert glycerol into the intermediate of glycolysis DHAP (dihydroxyacetone phosphate), cloning of the glycerol dehydrogenase gene (Gcy), the dihydroxyacetone kinase gene (Dak) and the glycerol uptake protein gene (Gup1) was performed with reference to the nucleotide sequences of peptide regions from the genomic DNA (BY4741) of *Saccharomyces cerevisiae*.

Figure 2A:
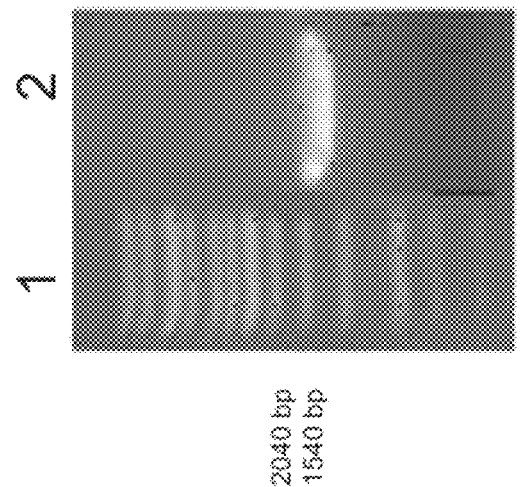
FIG. 2(A) shows the PCR product of the glycerol dehydrogenase gene (lane 1: 1-kb DNA marker; and lane 2, Gcy PCR product)
Figure 2B:
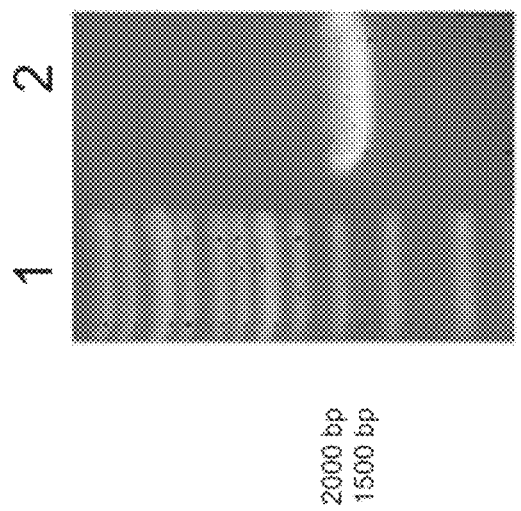
FIG. 2(B) shows the PCR product of the dihydroxyacetone kinase gene (lane 1: 1-kb DNA marker; and lane 2: Dak PCR product)
Figure 2C:
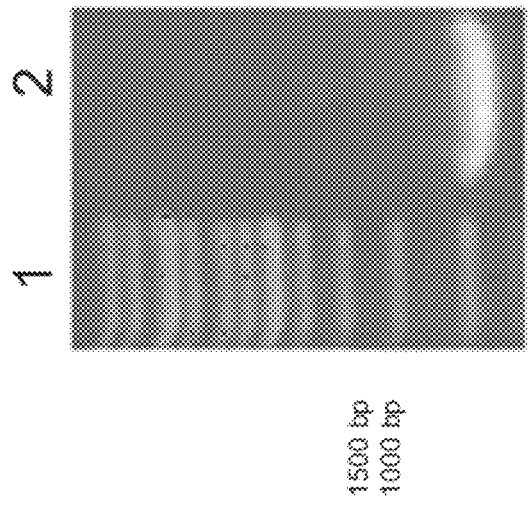
FIG. 2(C) shows the PCR product of the glycerol uptake protein gene (lane 1: 1-kb DNA marker; and lane 2: Gup PCR product).

For cloning of Gcy, Dak and Gup1, primers including the following recognition sequences were synthesized: for Gcy, BamH (5-ggatccatgcctgctactttacatgattct-3; SEQ ID NO: 13), Sal (5-gtcgacatacttgaatacttcgaaaggag-3); for Dak, Spe (5-actagtatgtccgctaaatcgtttgaagtc-3, SEQ ID NO: 14), and Cla (5-atcgatatacaaggcgctttgaacccccctt-3, SEQ ID NO: 15); and for Gup1, EcoR (5-gaattcatgtcgctgatcagcatcctg-3, SEQ ID NO: 16), and Spe (5-actagtccagcattttaggtaaattccgtg-3, SEQ ID NO: 17). Using the synthesized primers, PCR was performed for each gene under the following conditions: step 1 at 95° C. for 10 min; step 2 at 95° C. for 30 sec; step 3 at 50° C. for 30 sec; step 4 at 72° C. for 2 min; and step 5 at 95° C. for 10 min; the process from step 2 to step 4 being repeated for 30 cycles. As a result, PCR bands having lengths of 936 bp, 1755 bp and 1683 bp, respectively, could be confirmed (FIG. 2).

2. Cloning of Glycerol Dehydrogenase Gene, a Dihydroxyacetone Kinase Gene and a Glycerol Uptake Protein Gene Each of the Gcy, Dak and Gup amplification products obtained in Example 3-1 was electrophoresed on 0.8% agarose gel, and the DNA fragments on the agarose gels were collected using a Biospin gel extraction kit (Bioflux).

Then, Gcy, Dak and Gup1 were digested with BamH and Sal, Spe and Cla, and EcoR and Spe, respectively, after which each of the digested genes was ligated with the yeast-*E. coli* shuttle vector pESC-trp (Clontech) and transformed into *E. coli* DH5a. Then, the ligated recombinant plasmid DNAs were separated from the transformants. The recombinant vectors were named "pGcy", "pDak" and "pGup1", respectively.

Figure 3B:
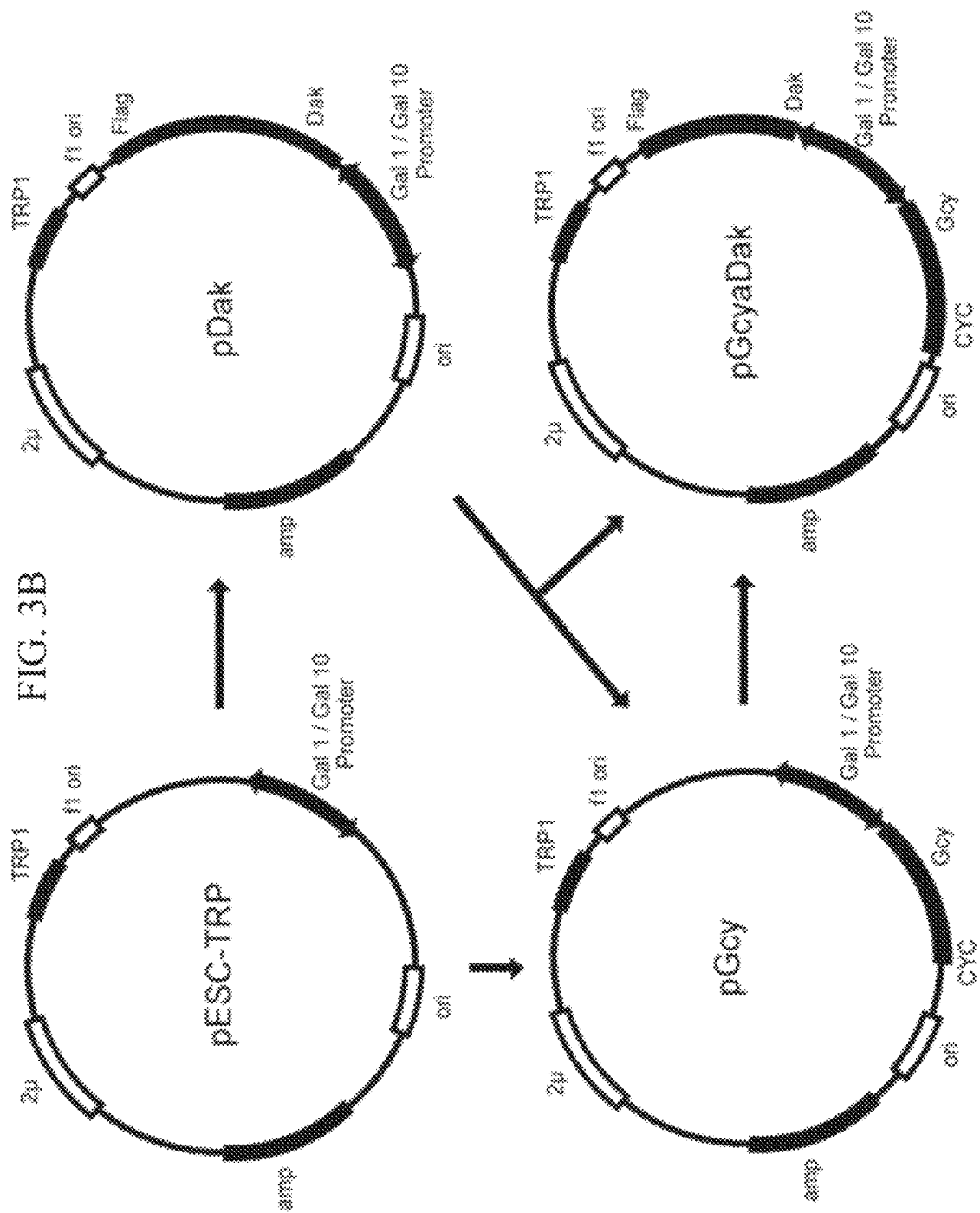
FIG. 3b is a schematic diagram showing the process of constructing the recombinant vector pGcyaDak containing glycerol dehydrogenase gene and a dihydroxyacetone kinase gene in both sense and antisense directions according to the present invention.

Next, Dak was cloned with the pGcy vector and transformed into *E. coli* DH5a (Invitrogen). From the transformant, the ligated recombinant plasmid DNA was separated. The recombinant vector was named "pGcyaDak", and is shown in FIG. 3b.

Figure 3C:
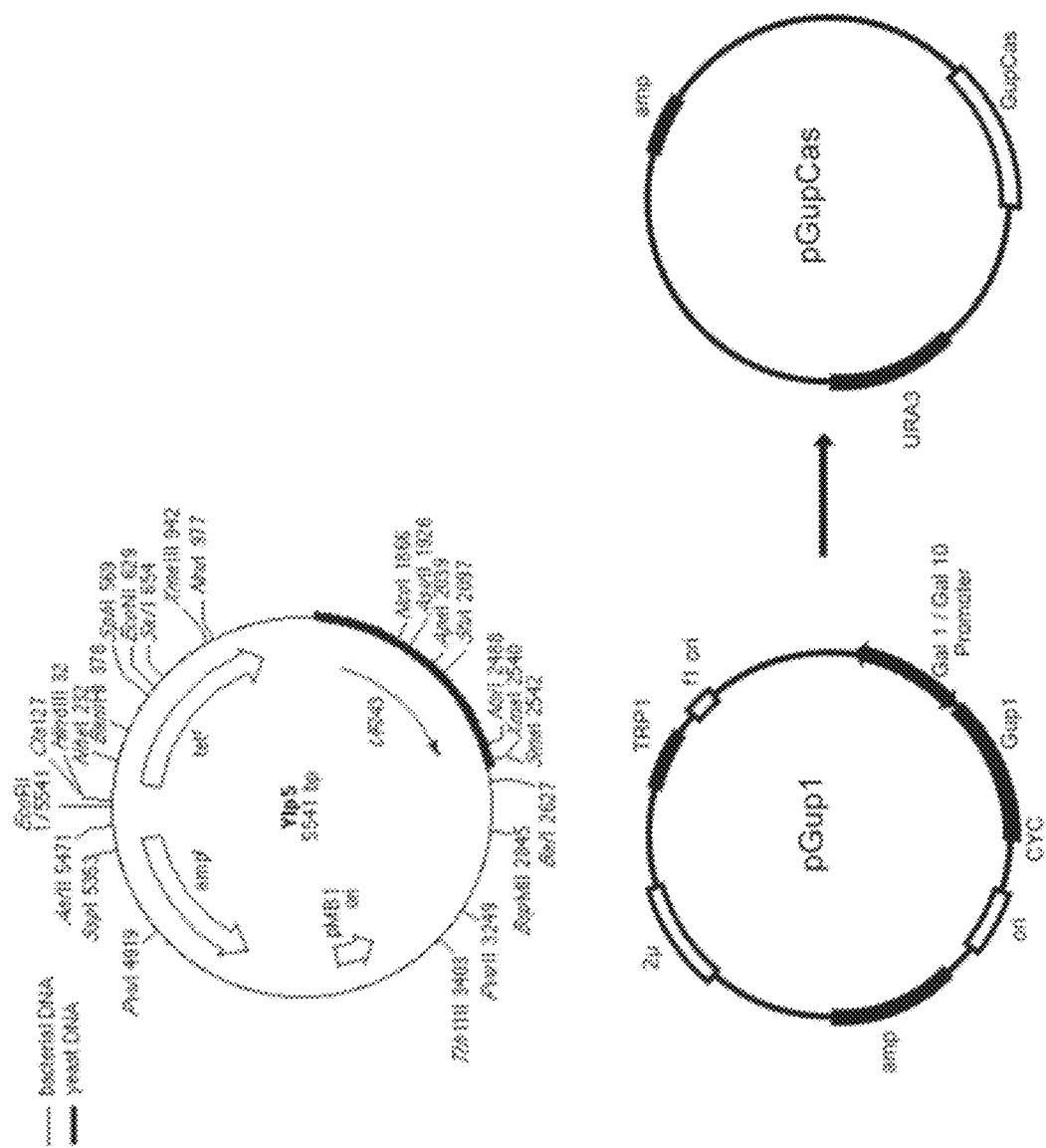
FIG. 3c is a schematic diagram showing the process of constructing the recombinant vector pGupCas containing a glycerol uptake protein gene according to the present invention.

Also, in order to insert pGup1 into the genomic DNA of *Saccharomyces cerevisiae*, a sense primer (5'-ggatccatgt cag-cattttaggtaaattccgtg-3', SEQ ID NO: 18) and an antisense primer (5'-ggatccataatgtcgctgatcagcatcctgtct-3', SEQ ID NO: 19) were constructed so as to include a BamH1 recognition sequence, and were cloned into the yeast integration vector YIP-5, which was then inserted into the genomic DNA of *Saccharomyces cerevisiae*. The resulting recombinant vector was named "pGupCas", and is shown in FIG. 3c.

Example 4

Construction of Transformant *Saccharomyces cerevisiae* YPH499 (pGcyaDak, pGup1a Ws.Dgat Cas)

Yeast host cells were transformed with the above recombinant vectors (pGcyaDak, and pGup1a ws.dgat cas) according to the experimental method provided in the YEAST-MAKER yeast transformation kit2 (Clontech). The resulting transformant was named "*Saccharomyces cerevisiae* YPH499 (pGup1a ws.dgat cas)".

The yeast host cells used were *Saccharomyces cerevisiae* YPH499 (*S. cerevisiae* YPH499, ura3-52lys2-801am-berade2-101ochretrpl-63 his3-200 leu2-1). Then, the transformant was selected using a tryptophan-deficient SD medium (0.67% yeast nitrogen base, 2% glucose, 0.067% yeast nitrogen base w/o trp, 2% agar), and also the strain comprising Gup1 inserted into *Saccharomyces cerevisiae* YPH499 was selected in an SD medium containing G418 (100 ug/ml). The selected strain was deposited at the Korean Culture Center of Microorganisms (KCCM) on 18 Aug., 2010 and was assigned accession number KCCM11094P.

Example 5

Examination of Conditions for Culture of Transformant *Saccharomyces cerevisiae* YPH499 (pGcyaDak, pGup1a Ws.Dgat Cas)

In order to examine the synthesis of fatty acid ethyl esters caused by the addition of sodium oleate (short chain fatty acid) during the culture of the transformant *Saccharomyces cerevisiae* YPH499 (pGcyaDak, pGup1a ws.dgat cas), the synthesis of ethanol and fatty acid ester in each of media (0.67% yeast nitrogen base, 2% glycerol, 0.067% yeast nitrogen base w/o trp, 0.2% galactose, 2% agar) containing or not containing sodium oleate was measured. The constructed transformant was cultured for 96 hours in each of a medium containing 0.1% sodium oleate and a medium not containing sodium oleate, and was then analyzed by GC-MS.

Figure 4A:
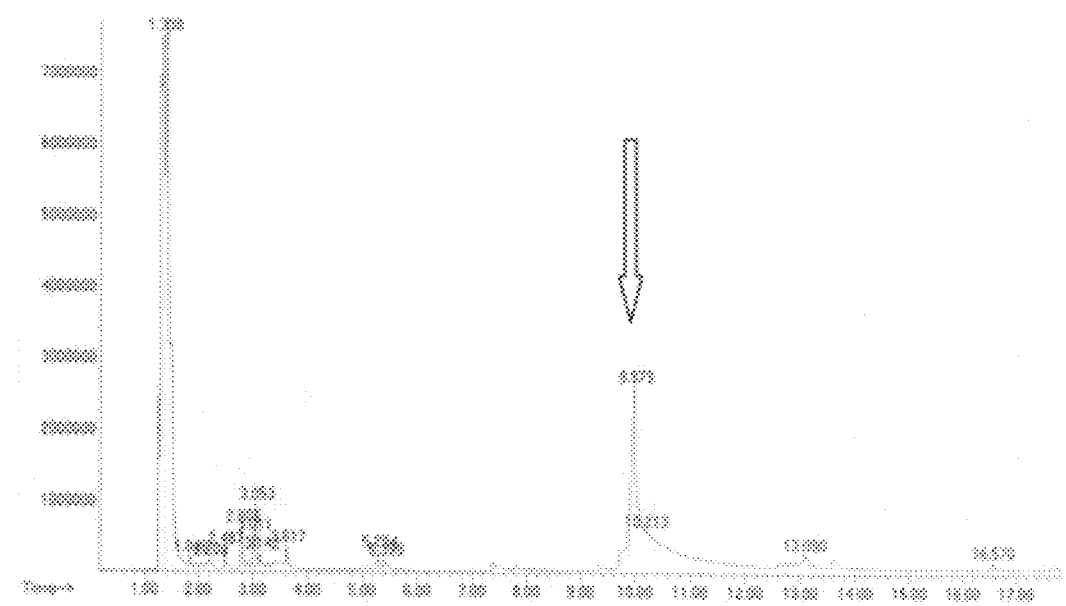
FIG. 4 shows the results of GC-MS analysis before (a) and after (b) the addition of oleate.
Figure 4B:
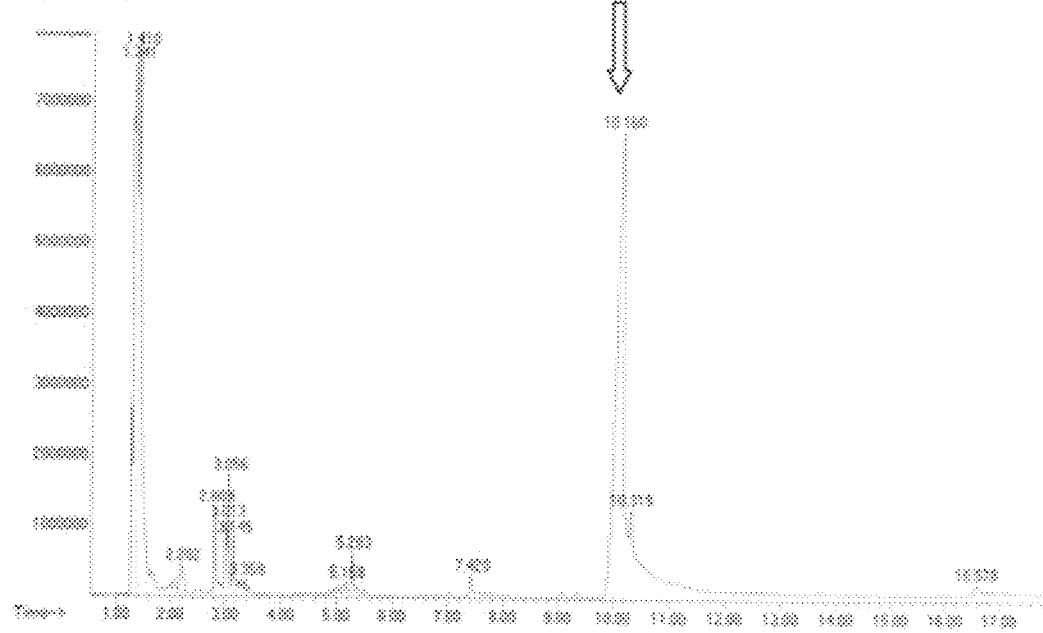

The analysis results are shown in FIG. 4, which shows the results of analysis of the components of the produced fatty acid ethyl esters by GC-MS. The results in FIG. 4 indicate that the most major component of the fatty acid ethyl esters was ethyl oleate and that fatty acid ethyl esters were successfully produced in the transformant constructed according to the present invention.

Example 6

Production of Fatty Acid Ethyl Esters in Transformant *Saccharomyces cerevisiae* YPH499 (pGcyaDak, pGup1a Ws.Dgat Cas)

Figure 5A:
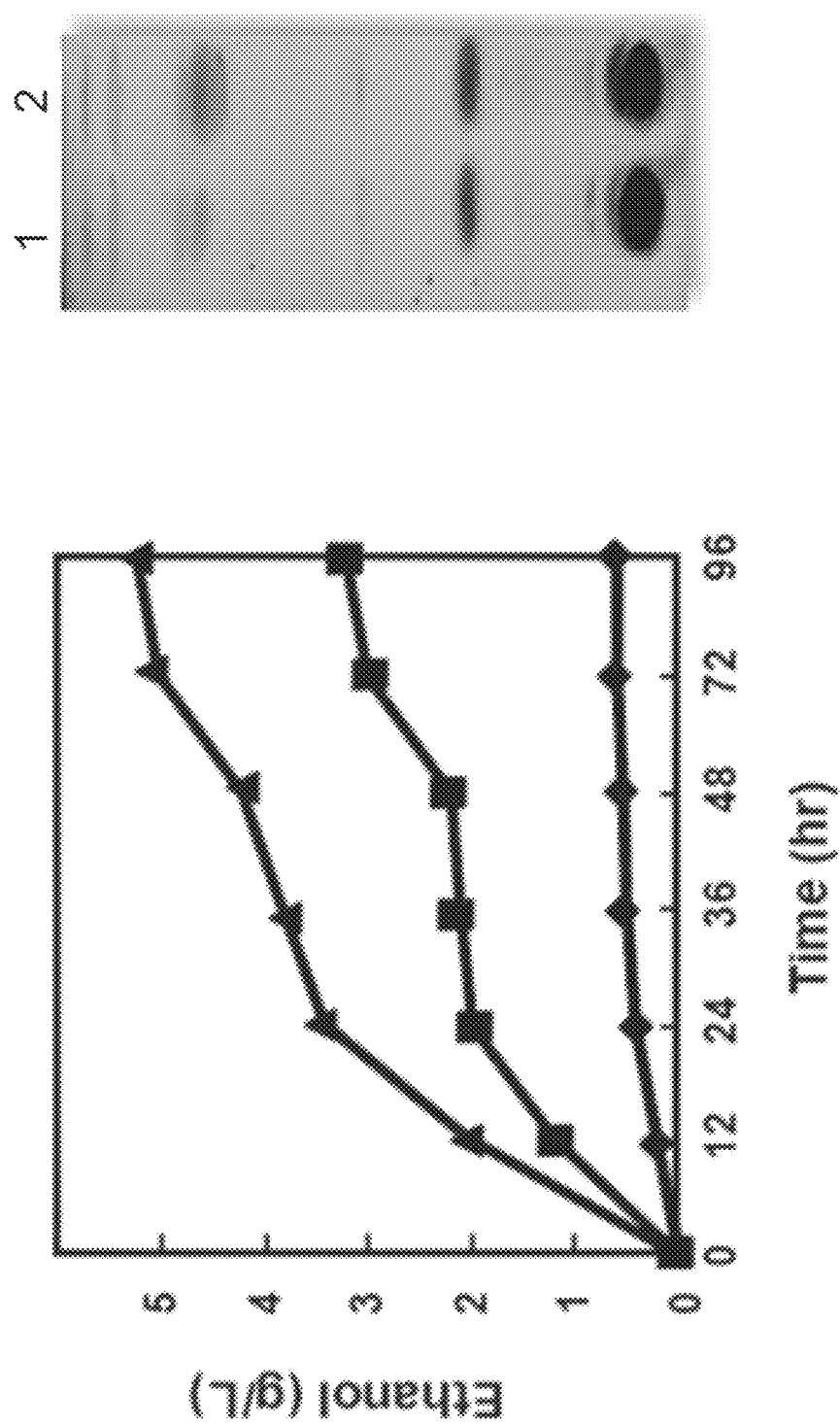
FIG. 5a shows the results of measuring the synthesis of ethanol (left) and fatty acid ethyl esters (right) when the transformant containing the ws/dgat-encoding gene according to the present invention was cultured in a medium not containing sodium oleate.
Figure 5B:
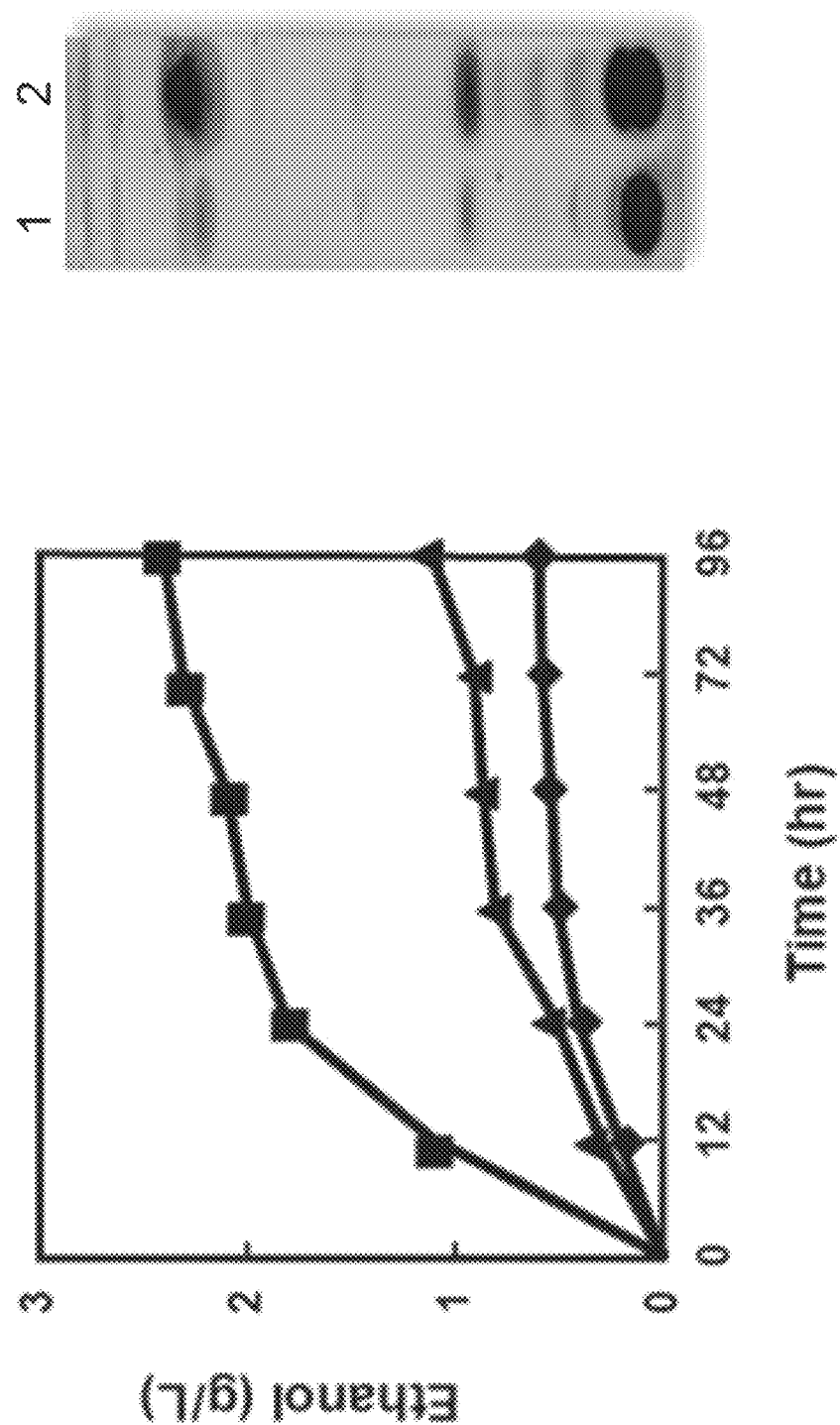
FIG. 5b shows the results of measuring the synthesis of ethanol (left) and fatty acid ethyl esters (right) when the transformant containing the ws/dgat-encoding gene according to the present invention was cultured in a medium containing sodium oleate.

Each of YPH499 (pESC-TRP), YPH499 (pGcyaDak, pGupCas) and YPH499 (pGcyaDak, pGup1a ws.dgat cas) was precultured for 24 hours in an SG medium (0.67% yeast nitrogen base, 2% glucose, 0.067% yeast nitrogen base w/o trp, 0.2% galactose) inducing expression by galactose, and was then shake-cultured for 48 hours in a fermentation medium (0.67% yeast nitrogen base, 2% glycerol, 0.067% yeast nitrogen base w/o trp, 0.2% galactose) containing 2% glycerol as a substrate, until the absorbance of the medium at a wavelength of 600 nm reached 1. The fermentation broth was cultured in each of media containing sodium oleate and not containing sodium oleate, at 30° C. and 100 rpm, while the culture broth was sampled at various time points and subjected to gas chromatography, thereby measuring the amount of ethanol produced. Also, the production of fatty acid ethyl esters (oleic acid ethyl ester) was measured by TLC (FIG. 5 *a*). It was found that, when the strains were cultured so as to produce fatty acid ethyl esters, the synthesis of fatty acid ethyl esters was possible in the medium containing 0.1% sodium oleate. The measurement results are shown in FIG. 5*b*. FIG. 5 shows the dependence of the transformant of the present invention on oleate. Specifically, FIG. 5*a* shows that, when no oleate was added during culture, fatty acid ethyl esters were not produced, and FIG. 5*b* shows that, when oleate was added, fatty acid ethyl esters were successfully produced by efficiently using ethanol produced in the transformant of the present invention.

The invention claimed is:

1. A transformant that is *Saccharomyces cerevisiae* YPH499 (pGcyaDak, pGup1a ws.dgat cas) (accession number: KCCM11094P).

2. A method for preparing a transformant for producing fatty acid ethyl esters, the method comprising the steps of:
constructing a recombinant vector comprising a gene encoding ws/dgat (wax ester synthase/acyl-coenzyme A: diacylglycerol acyltransferase) and a glycerol uptake protein gene;
constructing a recombinant vector comprising a glycerol dehydrogenase gene and a dihydroxyacetone kinase gene; and
transforming *Saccharomyces cerevisiae* YPH499 with the recombinant vectors, wherein the transformant is *Saccharomyces cerevisiae* YPH499(pGcyaDak, pGup1 a ws.dgat cas) (accession number: KCCM11094P).

3. A method for producing fatty acid ethyl esters, comprising a step of culturing the transformant of claim 1 using glycerol as a substrate.

4. The method of claim 3, wherein the glycerol is a byproduct of biodiesel production.

5. The method of claim 3 wherein a fatty acid salt having 12 to 20 carbon atoms is added during the culturing step.

6. The method of claim 3, wherein the culturing step is carried out at a temperature ranging from 25° C. to 30° C.

* * * * *

SEQUENCE LISTING

```
<160> NUMBER OF SEQ ID NOS: 19

<210> SEQ ID NO 1
<211> LENGTH: 458
<212> TYPE: PRT
<213> ORGANISM: Acinetobacter sp.

<400> SEQUENCE: 1

Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Phe Asp Leu Asp His His Phe Arg
65                  70                  75                  80

His Ile Ala Leu Pro His Pro Gly Arg Ile Arg Glu Leu Leu Ile Tyr
            85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205
```

```
Ile Gly Arg Asn Pro Asp His Val Ser Ser Phe Gln Ala Pro Cys Ser
    210                 215                 220

Ile Leu Asn Gln Arg Val Ser Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
                260                 265                 270

Leu Met Ser His Asn Ser Leu Pro Ser Lys Pro Leu Ile Ala Met Val
        275                 280                 285

Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
                340                 345                 350

Pro Ala Gly Leu Asn Ile Ile Ser Gly Met Met Pro Lys Arg Gln Ala
        355                 360                 365

Phe Asn Leu Val Ile Ser Asn Val Pro Gly Pro Arg Glu Pro Leu Tyr
    370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
                420                 425                 430

Leu Leu Thr His Leu Glu Glu Glu Ile Gln Leu Phe Glu Gly Val Ile
        435                 440                 445

Ala Lys Gln Glu Asp Ile Lys Thr Ala Asn
    450                 455

<210> SEQ ID NO 2
<211> LENGTH: 1377
<212> TYPE: DNA
<213> ORGANISM: Acinetobacter sp.

<400> SEQUENCE: 2
atgcgcccat tacatccgat tgattttata ttcctgtcac tagaaaaaag acaacagcct    60
atgcatgtag gtggtttatt tttgtttcag attcctgata acgccccaga caccttatt   120 caagatctgg tgaatgatat ccggatatca aaatcaatcc ctgttccacc attcaacaat   180
aaactgaatg ggcttttttg ggatgaagat gaagagtttg atttagatca tcattttcgt   240
catattgcac tgcctcatcc tggtcgtatt cgtgaattgc ttatttatat ttcacaagag   300
cacagtacgc tgctagatcg ggcaaagccc ttgtggacct gcaatattat tgaaggaatt   360
gaaggcaatc gttttgccat gtacttcaaa attcaccatg cgatggtcga tggcgttgct   420
ggtatgcggt taattgaaaa atcactctcc catgatgtaa cagaaaaaag tatcgtgcca   480
ccttggtgtg ttgagggaaa acgtgcaaag cgcttaagag aacctaaaac aggtaaaatt   540
aagaaaatca tgtctggtat taagagtcag cttcaggcga cacccacagt cattcaagag   600
ctttctcaga cagtatttaa agatattgga cgtaatcctg atcatgtttc aagctttcag   660
gcgccttgtt ctattttgaa tcagcgtgtg agctcatcgc gacgttttgc agcacagtct   720
```

-continued

```
tttgacctag atcgttttcg taatattgcc aaatcgttga atgtgaccat taatgatgtt      780
gtactagcgg tatgttctgg tgcattacgt gcgtatttga tgagtcataa tagttttgcct    840 tcaaaaccat taattgccat ggttccagcc tctattcgca atgacgattc agatgtcagc    900
aaccgtatta cgatgattct ggcaaatttg gcaacccaca aagatgatcc tttacaacgt    960
cttgaaatta tccgccgtag tgttcaaaac tcaaagcaac gcttcaaacg tatgaccagc   1020
gatcagattc taaattatag tgctgtcgta tatggccctg caggactcaa cataatttct   1080
ggcatgatgc aaaacgcca agccttcaat ctggttattt ccaatgtgcc tggcccaaga   1140
gagccacttt actggaatgg tgccaaactt gatgcactct acccagcttc aattgtatta   1200
gacggtcaag cattgaatat tacaatgacc agttatttag ataaacttga agttggtttg   1260
attgcatgcc gtaatgcatt gccaagaatg cagaatttac tgacacattt agaagaagaa   1320
attcaactat ttgaaggcgt aattgcaaag caggaagata ttaaaacagc caattaa      1377
```

<210> SEQ ID NO 3
<211> LENGTH: 312
<212> TYPE: PRT
<213> ORGANISM: Artificial Sequence
<220> FEATURE:
<223> OTHER INFORMATION: glycerol dehydrogenase

<400> SEQUENCE: 3

```
Met Pro Ala Thr Leu His Asp Ser Thr Lys Ile Leu Ser Leu Asn Thr
1               5                   10                  15

Gly Ala Gln Ile Pro Gln Ile Gly Leu Gly Thr Trp Gln Ser Lys Glu
            20                  25                  30

Asn Asp Ala Tyr Lys Ala Val Leu Thr Ala Leu Lys Asp Gly Tyr Arg
        35                  40                  45

His Ile Asp Thr Ala Ala Ile Tyr Arg Asn Glu Asp Gln Val Gly Gln
    50                  55                  60

Ala Ile Lys Asp Ser Gly Val Pro Arg Glu Glu Ile Phe Val Thr Thr
65                  70                  75                  80

Lys Leu Trp Cys Thr Gln His His Glu Pro Glu Val Ala Leu Asp Gln
                85                  90                  95

Ser Leu Lys Arg Leu Gly Leu Asp Tyr Val Asp Leu Tyr Leu Met His
            100                 105                 110

Trp Pro Ala Arg Leu Asp Pro Ala Tyr Ile Lys Asn Glu Asp Ile Leu
        115                 120                 125

Ser Val Pro Thr Lys Lys Asp Gly Ser Arg Ala Val Asp Ile Thr Asn
    130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Leu
                165                 170                 175

Lys Asp Leu Leu Ala Ser Gln Gly Asn Lys Leu Thr Pro Ala Ala Asn
            180                 185                 190

Gln Val Glu Ile His Pro Leu Leu Pro Gln Asp Glu Leu Ile Asn Phe
        195                 200                 205

Cys Lys Ser Lys Gly Ile Val Val Glu Ala Tyr Ser Pro Leu Gly Ser
    210                 215                 220

Thr Asp Ala Pro Leu Leu Lys Glu Pro Val Ile Leu Glu Ile Ala Lys
225                 230                 235                 240

Lys Asn Asn Val Gln Pro Gly His Val Val Ile Ser Trp His Val Gln
                245                 250                 255
```

```
Arg Gly Tyr Val Val Leu Pro Lys Ser Val Asn Pro Asp Arg Ile Lys
            260                 265                 270

Thr Asn Arg Lys Ile Phe Thr Leu Ser Thr Glu Asp Phe Glu Ala Ile
        275                 280                 285

Asn Asn Ile Ser Lys Glu Lys Gly Glu Lys Arg Val Val His Pro Asn
    290                 295                 300

Trp Ser Pro Phe Glu Val Phe Lys
305                 310

<210> SEQ ID NO 4
<211> LENGTH: 939
<212> TYPE: DNA
<213> ORGANISM: Artificial Sequence
<220> FEATURE:
<223> OTHER INFORMATION: glycerol dehydrogenase gene

<400> SEQUENCE: 4
atgcctgcta ctttacatga ttctacgaaa atcctttctc taaatactgg agcccaaatc      60
cctcaaatag gtttaggtac gtggcagtcg aaagagaacg atgcttataa ggctgtttta     120
accgctttga agatggcta ccgacacatt gatactgctg ctatttaccg taatgaagac     180
caagtcggtc aagccatcaa ggattcaggt gttcctcggg aagaaatctt tgttactaca     240
aagttatggt gtacacaaca ccacgaacct gaagtagcgc tggatcaatc actaaagagg     300
ttaggattgg actacgtaga cttatatttg atgcattggc ctgccagatt agatccagcc     360
tacatcaaaa atgaagacat cttgagtgtg ccaacaaaga aggatggttc tcgtgcagtg     420
gatatcacca attggaattt catcaaaacc tgggaattaa tgcaggaact accaaagact     480
ggtaaaacta aggccgttgg agtctccaac ttttctataa ataacctgaa agatctatta     540
gcatctcaag gtaataagct tacgccagct gctaaccaag tcgaaataca tccattacta     600
cctcaagacg aattgattaa ttttttgtaaa agtaaaggca ttgtggttga agcttattct     660
ccgttaggta gtaccgatgc tccactattg aaggaaccgg ttatccttga aattgcgaag     720
aaaaataacg ttcaacccgg acacgttgtt attagctggc acgtccaaag aggttatgtt     780
gtcttgccaa atctgtgaa tcccgatcga atcaaaacga acaggaaaat atttactttg     840
tctactgagg actttgaagc tatcaataac atatcgaagg aaaagggcga aaaagggtt     900 gtacatccaa attggtctcc tttcgaagta ttcaagtaa                              939

<210> SEQ ID NO 5
<211> LENGTH: 584
<212> TYPE: PRT
<213> ORGANISM: Artificial Sequence
<220> FEATURE:
<223> OTHER INFORMATION: dihydroxyacetone kinase

<400> SEQUENCE: 5

Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
            20                  25                  30

Lys Ile Leu Phe Arg Lys Thr Asp Ser Asp Lys Ile Ala Leu Ile Ser
        35                  40                  45

Gly Gly Gly Ser Gly His Glu Pro Thr His Ala Gly Phe Ile Gly Lys
    50                  55                  60

Gly Met Leu Ser Gly Ala Val Val Gly Glu Ile Phe Ala Ser Pro Ser
65                  70                  75                  80
```

```
Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
        115                 120                 125

Ala Val Ile Gly Asp Asp Val Ala Val Gly Arg Glu Lys Gly Gly Met
    130                 135                 140

Val Gly Arg Arg Ala Leu Ala Gly Thr Val Leu Val His Lys Ile Val
145                 150                 155                 160

Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
            180                 185                 190

Ser Leu Asp His Cys Lys Val Pro Gly Arg Lys Phe Glu Ser Glu Leu
        195                 200                 205

Asn Glu Lys Gln Met Glu Leu Gly Met Gly Ile His Asn Glu Pro Gly
210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255

Val Lys Phe Asp Glu Asp Asp Glu Val Val Leu Leu Val Asn Asn Leu
            260                 265                 270

Gly Gly Val Ser Asn Phe Val Ile Ser Ser Ile Thr Ser Lys Thr Thr
        275                 280                 285

Asp Phe Leu Lys Glu Asn Tyr Asn Ile Thr Pro Val Gln Thr Ile Ala
    290                 295                 300

Gly Thr Leu Met Thr Ser Phe Asn Gly Asn Gly Phe Ser Ile Thr Leu
305                 310                 315                 320

Leu Asn Ala Thr Lys Ala Thr Lys Ala Leu Gln Ser Asp Phe Glu Glu
                325                 330                 335

Ile Lys Ser Val Leu Asp Leu Leu Asn Ala Phe Thr Asn Ala Pro Gly
            340                 345                 350

Trp Pro Ile Ala Asp Phe Glu Lys Thr Ser Ala Pro Ser Val Asn Asp
        355                 360                 365

Asp Leu Leu His Asn Glu Val Thr Ala Lys Ala Val Gly Thr Tyr Asp
    370                 375                 380

Phe Asp Lys Phe Ala Glu Trp Met Lys Ser Gly Ala Glu Gln Val Ile
385                 390                 395                 400

Lys Ser Glu Pro His Ile Thr Glu Leu Asp Asn Gln Val Gly Asp Gly
                405                 410                 415

Asp Cys Gly Tyr Thr Leu Val Ala Gly Val Lys Gly Ile Thr Glu Asn
            420                 425                 430

Leu Asp Lys Leu Ser Lys Asp Ser Leu Ser Gln Ala Val Ala Gln Ile
        435                 440                 445

Ser Asp Phe Ile Glu Gly Ser Met Gly Gly Thr Ser Gly Gly Leu Tyr
    450                 455                 460

Ser Ile Leu Leu Ser Gly Phe Ser His Gly Leu Ile Gln Val Cys Lys
465                 470                 475                 480

Ser Lys Asp Glu Pro Val Thr Lys Glu Ile Val Ala Lys Ser Leu Gly
                485                 490                 495

Ile Ala Leu Asp Thr Leu Tyr Lys Tyr Thr Lys Ala Arg Lys Gly Ser
            500                 505                 510
```

```
Ser Thr Met Ile Asp Ala Leu Glu Pro Phe Val Lys Glu Phe Thr Ala
        515                 520                 525
Ser Lys Asp Phe Asn Lys Ala Val Lys Ala Ala Glu Glu Gly Ala Lys
    530                 535                 540
Ser Thr Ala Thr Phe Glu Ala Lys Phe Gly Arg Ala Ser Tyr Val Gly
545                 550                 555                 560
Asp Ser Ser Gln Val Glu Asp Pro Gly Ala Val Gly Leu Cys Glu Phe
            565                 570                 575
Leu Lys Gly Val Gln Ser Ala Leu
        580

<210> SEQ ID NO 6
<211> LENGTH: 1755
<212> TYPE: DNA
<213> ORGANISM: Artificial Sequence
<220> FEATURE:
<223> OTHER INFORMATION: dihydroxyacetone kinase gene

<400> SEQUENCE: 6
atgtccgcta atcgtttga agtcacagat ccagtcaatt caagtctcaa agggtttgcc      60
cttgctaacc cctccattac gctggtccct gaagaaaaaa ttctcttcag aaagaccgat    120
tccgacaaga tcgcattaat ttctggtggt ggtagtggac atgaacctac acacgccggt    180
ttcattggta agggtatgtt gagtggcgcc gtggttggcg aaattttgc atccccttca     240
acaaaacaga ttttaaatgc aatccgttta gtcaatgaaa atgcgtctgg cgttttattg    300
attgtgaaga actacacagg tgatgttttg cattttggtc tgtccgctga gagagcaaga    360
gccttgggta ttaactgccg cgttgctgtc ataggtgatg atgttgcagt tggcagagaa    420
aagggtggta tggttggtag aagagcattg gcaggtaccg ttttggttca taagattgta    480
ggtgccttcg cagaagaata ttctagtaag tatggcttag acggtacagc taaagtggct    540
aaaattatca cgacaatttt ggtgaccatt ggatcttctt tagaccattg taaagttcct    600
ggcaggaaat tcgaaagtga attaaacgaa aaacaaatgg aattgggtat gggtattcat    660
aacgaacctg gtgtgaaagt tttagaccct attccttcta ccgaagactt gatctccaag    720
tatatgctac caaaactatt ggatccaaac gataaggata gagcttttgt aaagtttgat    780
gaagatgatg aagttgtctt gttagttaac aatctcggcg gtgtttctaa ttttgttatt    840
agttctatca cttccaaaac tacggatttc ttaaaggaaa attacaacat aaccccggtt    900
caaacaattg ctggcacatt gatgacctcc ttcaatggta atgggttcag tatcacatta    960
ctaaacgcca ctaaggctac aaaggctttg caatctgatt ttgaggagat caaatcagta   1020
ctagacttgt tgaacgcatt tacgaacgca ccgggctggc caattgcaga ttttgaaaag   1080
acttctgccc catctgttaa cgatgacttg ttacataatg aagtaacagc aaaggccgtc   1140
ggtacctatg actttgacaa gtttgctgag tggatgaaga gtggtgctga acaagttatc   1200
aagagcgaac cgcacattac ggaactagac aatcaagttg gtgatggtga ttgtggttac   1260
actttagtgg caggagttaa aggcatcacc gaaaaccttg acaagctgtc gaaggactca   1320
ttatctcagg cggttgccca aatttcagat ttcattgaag gctcaatggg aggtactttct  1380
ggtggtttat attctattct tttgtcgggt ttttcacacg gattaattca ggtttgtaaa   1440
tcaaaggatg aacccgtcac taaggaaatt gtggctaagt cactcggaat tgcattggat   1500
actttataca aatatacaaa ggcaaggaag ggatcatcca ccatgattga tgctttagaa   1560
ccattcgtta agaatttac tgcatctaag gatttcaata aggcggtaaa agctgcagag   1620
gaaggtgcta aatccactgc tacattcgag gccaaatttg gcagagcttc gtatgtcggc   1680
```

-continued

```
gattcatctc aagtagaaga tcctggtgca gtaggcctat gtgagttttt gaagggggtt    1740
caaagcgcct tgtaa                                                    1755
```

<210> SEQ ID NO 7
<211> LENGTH: 560
<212> TYPE: PRT
<213> ORGANISM: Artificial Sequence
<220> FEATURE:
<223> OTHER INFORMATION: glycerol uptake protein

<400> SEQUENCE: 7

```
Met Ser Leu Ile Ser Ile Leu Ser Pro Leu Ile Thr Ser Glu Gly Leu
1               5                   10                  15

Asp Ser Arg Ile Lys Pro Ser Pro Lys Lys Asp Ala Ser Thr Thr Thr
            20                  25                  30

Lys Pro Ser Leu Trp Lys Thr Thr Glu Phe Lys Phe Tyr Tyr Ile Ala
        35                  40                  45

Phe Leu Val Val Val Pro Leu Met Phe Tyr Ala Gly Leu Gln Ala Ser
    50                  55                  60

Ser Pro Glu Asn Pro Asn Tyr Ala Arg Tyr Glu Arg Leu Leu Ser Gln
65                  70                  75                  80

Gly Trp Leu Phe Gly Arg Lys Val Asp Asn Ser Asp Ser Gln Tyr Arg
                85                  90                  95

Phe Phe Arg Asp Asn Phe Ala Leu Leu Ser Val Leu Met Leu Val His
            100                 105                 110

Thr Ser Ile Lys Arg Ile Val Leu Tyr Ser Thr Asn Ile Thr Lys Leu
        115                 120                 125

Arg Phe Asp Leu Ile Phe Gly Leu Ile Phe Leu Val Ala Ala His Gly
    130                 135                 140

Val Asn Ser Ile Arg Ile Leu Ala His Met Leu Ile Leu Tyr Ala Ile
145                 150                 155                 160

Ala His Val Leu Lys Asn Phe Arg Arg Ile Ala Thr Ile Ser Ile Trp
                165                 170                 175

Ile Tyr Gly Ile Ser Thr Leu Phe Ile Asn Asp Asn Phe Arg Ala Tyr
            180                 185                 190

Pro Phe Gly Asn Ile Cys Ser Phe Leu Ser Pro Leu Asp His Trp Tyr
        195                 200                 205

Arg Gly Ile Ile Pro Arg Trp Asp Val Phe Phe Asn Phe Thr Leu Leu
    210                 215                 220

Arg Val Leu Ser Tyr Asn Leu Asp Phe Leu Glu Arg Trp Glu Asn Leu
225                 230                 235                 240

Gln Lys Lys Lys Ser Pro Ser Tyr Glu Ser Lys Glu Ala Lys Ser Ala
                245                 250                 255

Ile Leu Leu Asn Glu Arg Ala Arg Leu Thr Ala Ala His Pro Ile Gln
            260                 265                 270

Asp Tyr Ser Leu Met Asn Tyr Ile Ala Tyr Val Thr Tyr Thr Pro Leu
        275                 280                 285

Phe Ile Ala Gly Pro Ile Ile Thr Phe Asn Asp Tyr Val Tyr Gln Ser
    290                 295                 300

Lys His Thr Leu Pro Ser Ile Asn Phe Lys Phe Ile Tyr Tyr Ala
305                 310                 315                 320

Val Arg Phe Val Ile Ala Leu Leu Ser Met Glu Phe Ile Leu His Phe
                325                 330                 335

Leu His Val Val Ala Ile Ser Lys Thr Lys Ala Trp Glu Asn Asp Thr
            340                 345                 350
```

```
Pro Phe Gln Ile Ser Met Ile Gly Leu Phe Asn Leu Asn Ile Ile Trp
            355                 360                 365

Leu Lys Leu Leu Ile Pro Trp Arg Leu Phe Arg Leu Trp Ala Leu Leu
    370                 375                 380

Asp Gly Ile Asp Thr Pro Glu Asn Met Ile Arg Cys Val Asp Asn Asn
385                 390                 395                 400

Tyr Ser Ser Leu Ala Phe Trp Arg Ala Trp His Arg Ser Tyr Asn Lys
                405                 410                 415

Trp Val Val Arg Tyr Ile Tyr Ile Pro Leu Gly Gly Ser Lys Asn Arg
                420                 425                 430

Val Leu Thr Ser Leu Ala Val Phe Ser Phe Val Ala Ile Trp His Asp
            435                 440                 445

Ile Glu Leu Lys Leu Leu Leu Trp Gly Trp Leu Ile Val Leu Phe Leu
    450                 455                 460

Leu Pro Glu Ile Phe Ala Thr Gln Ile Phe Ser His Tyr Thr Asp Ala
465                 470                 475                 480

Val Trp Tyr Arg His Val Cys Ala Val Gly Ala Val Phe Asn Ile Trp
                485                 490                 495

Val Met Met Ile Ala Asn Leu Phe Gly Phe Cys Leu Gly Ser Asp Gly
            500                 505                 510

Thr Lys Lys Leu Leu Ser Asp Met Phe Cys Thr Val Ser Gly Phe Lys
    515                 520                 525

Phe Val Ile Leu Ala Ser Val Ser Leu Phe Ile Ala Val Gln Ile Met
530                 535                 540

Phe Glu Ile Arg Glu Glu Lys Arg His Gly Ile Tyr Leu Lys Cys
545                 550                 555                 560

<210> SEQ ID NO 8
<211> LENGTH: 1683
<212> TYPE: DNA
<213> ORGANISM: Artificial Sequence
<220> FEATURE:
<223> OTHER INFORMATION: glycerol uptake protein gene

<400> SEQUENCE: 8
atgtcgctga tcagcatcct gtctcccta attacttccg agggcttaga ttcaagaatc      60
aaaccttcac caaaaaagga tgcctctact accactaagc catcactatg gaaaactact     120
gagttcaaat tctactacat tgcatttctg gtcgtggttc ccttgatgtt ctatgctggg     180
ttacaagcta gttcgcccga aaatccaaac tatgcaagat acgaacgtct cctatctcaa     240
ggttggttat ttggcagaaa agtagacaat agtgattctc aatataggtt ttcagggac      300 aattttgcgc tattgtcagt tttaatgcta gtccacactt ctataaaacg cattgtactt     360
tattcaacaa atatcactaa attgaggttt gatctgatat ttggtttgat ctttttagtg     420
gccgctcatg tgtcaattc gataagaatt ttagcccata tgctaatttt atatgccatc     480
gcccatgtac taagaacctt tagaagaata gccaccatca gcatttggat ttatggtatt     540
tctacgcttt ttattaacga caacttcaga gcatatccat tggtaatat ttgctctttt      600 ttaagcccat tggaccattg gtatagaggt atcattccaa gatgggatgt cttttttcaat    660 tttactcttt tgagagtctt aagttacaac ttggacttct tagagaggtg ggagaattta     720
caaaagaaga aaagtccatc ctatgaatca aagaagcta atcagccat tttgctcaat       780 gaacgtgcta gattaactgc tgcacacccc atacaggact acagcttaat gaattatatt     840
gcatatgtta cttacgcgcc acttttcatt gccggcccca ttataacatt caatgattat     900
gtttaccaat cgaaacatac cttgccatca ataaatttca aattcatttt ttactatgcg    960
```

```
gtgagattcg ttattgctct cttatctatg gagttcattt tacactttct ccacgttgtg    1020
gcaatctcaa aaaccaaagc gtgggaaaat gacacacctt tccagatttc catgattggc    1080
ttatttaatt tgaatattat ttggctaaaa ctactgattc cgtggaggct gtttaggctg    1140
tgggctttgc tagacggaat cgatacacct gaaaatatga tcaggtgtgt tgataacaat    1200
tacagttcac tagcattctg gagagcttgg catagaagct acaataagtg ggttgtccgt    1260
tacatatata ttcctctagg tggttcaaaa aatagagttt tgacatcact agcagtcttt    1320
tccttcgtag ctatatggca tgacatcgaa ctaaagttat tattatgggg ttggctaata    1380
gttttgttcc tcttaccaga aattttttgct acccaaattt tctctcatta taccgacgca    1440
gtctggtaca gacacgtttg cgctgtcggt gctgttttca acatatgggt tatgatgatc    1500
gctaatcttt ttggattctg cttgggctct gacggtacta aaaaattact aagcgatatg    1560
ttctgtaccg tatctggttt caaatttgta attttggcaa gcgttagttt attcatcgca    1620
gtacaaataa tgtttgaaat cagagaagaa gaaagaggc acggaattta cctaaaatgc    1680
tga                                                                  1683

<210> SEQ ID NO 9
<211> LENGTH: 44
<212> TYPE: DNA
<213> ORGANISM: Artificial Sequence
<220> FEATURE:
<223> OTHER INFORMATION: forward primer

<400> SEQUENCE: 9
actagtcccg ccgccaccaa ggagatgcgc ccattacatc cgat              44

<210> SEQ ID NO 10
<211> LENGTH: 30
<212> TYPE: DNA
<213> ORGANISM: Artificial Sequence
<220> FEATURE:
<223> OTHER INFORMATION: reverse primer

<400> SEQUENCE: 10
actagtttaa ttggctgttt taatatcttc                              30

<210> SEQ ID NO 11
<211> LENGTH: 33
<212> TYPE: DNA
<213> ORGANISM: Artificial Sequence
<220> FEATURE:
<223> OTHER INFORMATION: sense primer

<400> SEQUENCE: 11
ggatccatgt cagcatttta ggtaaattcc gtg                          33

<210> SEQ ID NO 12
<211> LENGTH: 33
<212> TYPE: DNA
<213> ORGANISM: Artificial Sequence
<220> FEATURE:
<223> OTHER INFORMATION: antisence primer

<400> SEQUENCE: 12
ggatccataa tgtcgctgat cagcatcctg tct                          33

<210> SEQ ID NO 13
<211> LENGTH: 30
<212> TYPE: DNA
<213> ORGANISM: Artificial Sequence
```

```
<220> FEATURE:
<223> OTHER INFORMATION: BamH

<400> SEQUENCE: 13
ggatccatgc ctgctacttt acatgattct                              30

<210> SEQ ID NO 14
<211> LENGTH: 30
<212> TYPE: DNA
<213> ORGANISM: Artificial Sequence
<220> FEATURE:
<223> OTHER INFORMATION: Spe

<400> SEQUENCE: 14
actagtatgt ccgctaaatc gtttgaagtc                              30

<210> SEQ ID NO 15
<211> LENGTH: 30
<212> TYPE: DNA
<213> ORGANISM: Artificial Sequence
<220> FEATURE:
<223> OTHER INFORMATION: Cla

<400> SEQUENCE: 15
atcgatatac aaggcgcttt gaacccccct                              30

<210> SEQ ID NO 16
<211> LENGTH: 27
<212> TYPE: DNA
<213> ORGANISM: Artificial Sequence
<220> FEATURE:
<223> OTHER INFORMATION: EcoR

<400> SEQUENCE: 16
gaattcatgt cgctgatcag catcctg                                 27

<210> SEQ ID NO 17
<211> LENGTH: 30
<212> TYPE: DNA
<213> ORGANISM: Artificial Sequence
<220> FEATURE:
<223> OTHER INFORMATION: Spe

<400> SEQUENCE: 17
actagtccag cattttaggt aaattccgtg                              30

<210> SEQ ID NO 18
<211> LENGTH: 33
<212> TYPE: DNA
<213> ORGANISM: Artificial Sequence
<220> FEATURE:
<223> OTHER INFORMATION: sense primer

<400> SEQUENCE: 18
ggatccatgt cagcatttta ggtaaattcc gtg                          33

<210> SEQ ID NO 19
<211> LENGTH: 33
<212> TYPE: DNA
<213> ORGANISM: Artificial Sequence
<220> FEATURE:
<223> OTHER INFORMATION: anti-sense primer

<400> SEQUENCE: 19
ggatccataa tgtcgctgat cagcatcctg tct                          33
```